(12) United States Patent
Lauffer et al.

(10) Patent No.: US 8,263,777 B2
(45) Date of Patent: *Sep. 11, 2012

(54) AMINOPYRAZOLE TRIAZOLOTHIADIAZOLE INHIBITOR OF C-MET PROTEIN KINASE

(75) Inventors: David J. Lauffer, Stow, MA (US); Pan Li, Lexington, MA (US); Stefanie Roeper, Cambridge, MA (US); Shereen Ibrahim, Cambridge, MA (US); Anuj K. Kuldipkumar, Medford, MA (US); Yi Shi, Natick, MA (US); David B. Miller, Jr., Waltham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,215

(22) Filed: May 24, 2011

(65) Prior Publication Data

US 2011/0294849 A1 Dec. 1, 2011

Related U.S. Application Data

(60) Provisional application No. 61/348,929, filed on May 27, 2010.

(51) Int. Cl.
*A61K 31/47* (2006.01)
*C07D 215/12* (2006.01)
(52) U.S. Cl. ........................................ 546/176; 514/314
(58) Field of Classification Search ........................ None
See application file for complete search history.

(56) References Cited

FOREIGN PATENT DOCUMENTS

| WO | 2007064797 A2 | 6/2007 |
|---|---|---|
| WO | 2008144767 A1 | 11/2008 |
| WO | 2010138665 A1 | 12/2010 |

OTHER PUBLICATIONS

PCT/US2011/037659 International Search Report, 2011.

*Primary Examiner* — Janet Andres
*Assistant Examiner* — Heidi Reese
(74) *Attorney, Agent, or Firm* — Daniel A. Pearson

(57) ABSTRACT

The present invention relates to anhydrous and hydrated forms of Compound 1, which are useful in the inhibition of c-Met protein kinase. The invention also provides pharmaceutically acceptable compositions comprising compounds of formula I and methods of using the compositions in the treatment of proliferative disorders.

(1)

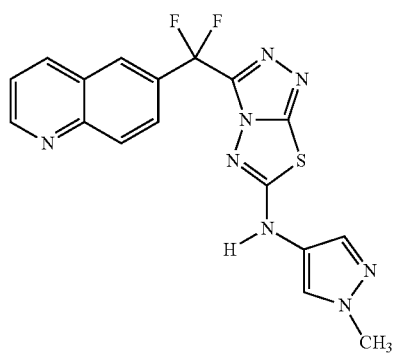

11 Claims, No Drawings

AMINOPYRAZOLE TRIAZOLOTHIADIAZOLE INHIBITOR OF C-MET PROTEIN KINASE

CROSS-REFERENCE TO RELATED APPLICATIONS

The present application claims the benefit, under 35 U.S.C. §119, to U.S. Provisional Application No. 61/348,929 filed May 27, 2010, the entire disclosures of which is incorporated herein by reference.

TECHNICAL FIELD OF THE INVENTION

The present invention relates to pharmaceutically useful forms of a selective inhibitor of c-Met and methods for their preparation.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase. c-Met, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-Met overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-Met is also implicated in atherosclerosis and lung fibrosis.

Accordingly, there is a great need to develop compounds useful as inhibitors of c-Met protein kinase receptor. In particular, preferred compounds should have high affinity to the c-Met receptor and show functional activity as antagonists, while showing little affinity for other kinase receptors or for targets known to be associated with adverse effects.

SUMMARY OF THE INVENTION

It has been found that 3-(difluoro(quinolin-6-yl)methyl)-N-(1-methyl-1H-pyrazol-4-yl)-[1,2,4]triazolo[3,4-b][1,3,4]thiadiazol-6-amine is an effective in the inhibition of c-Met.

Accordingly, the invention features anhydrous and hydrated forms of the following compound:

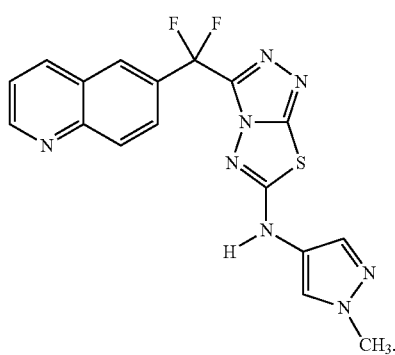

(1)

The invention also provides pharmaceutical compositions that include Compound 1 and a pharmaceutically acceptable carrier, adjuvant, or vehicle. Furthermore, the invention provides a method of preparing Compound 1. In addition, the invention provides methods of treating or lessening the severity of a proliferative disease, condition, or disorder in a patient that includes the step of administering to the patient a therapeutically effective dose of Compound 1, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, $75^{th}$ Ed. 1994. Additionally, general principles of organic chemistry are described in "Organic Chemistry," Thomas Sorrell, University Science Books, Sausalito: 1999, and "March's Advanced Organic Chemistry," $5^{th}$ Ed., Smith, M. B. and March, J., eds. John Wiley & Sons, New York: 2001, the entire contents of which are hereby incorporated by reference.

Description of the Compound of the Invention

In a first aspect, the invention features Compound 1:

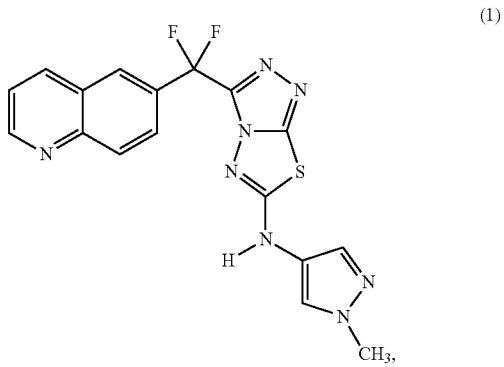

(1)

wherein the compound is anhydrous, with a crystalline form characterized by X-ray powder diffraction (XRPD) peaks at 5.0, 9.8, 12.9, 16.8, 19.3, 20.0, 21.2, 21.8, 22.5, 25.9, 26.2, 26.8, 28.5, 29.4, 30.7, 32.5, and 35.5 (2-theta scale).

In another aspect, the invention features Compound 1, wherein the compound is a dihydrate, with a crystalline form characterized by X-ray powder diffraction (XRPD) peaks at 6.1, 7.0, 8.0, 13.4, 13.9, 15.5, 18.1, 20.0, 21.1, 23.5, 23.7, 24.7, 26.4, and 27.0 (2-theta scale).

In another aspect, the invention features a method of preparing 3-(difluoro(quinolin-6-yl)methyl)-N-(heteroaryl)-[1,2,4]triazolo[3,4-b][1,3,4]thiadiazol-6-amines (e.g., Compound 1) that includes treating sodium 2,2-difluoro-2-(quinolin-6-yl)acetate with thiocarbohydrazine in the presence of propanephosphonic acid anhydride to produce 4-amino-5-(difluoro(quinolin-6-yl)methyl)-4H-1,2,4-triazole-3-thiol (compound 1004), followed by the reaction of compound 1004 with triphenylphosphine to produce 5-(difluoro(quinolin-6-yl)methyl)-4-(iminotriphenylphosphorano)-4H-1,2,4-triazole-3-thiol (compound 1005), followed by the reaction of compound 1005 with an isocyanto heteroaromatic compound (for example, 4-isocyanato-1-methyl-1H-pyrazole) to produce a 3-(difluoro(quinolin-6-yl)methyl)-N-(heteroaryl)-[1,2,4]triazolo[3,4-b][1,3,4]thiadiazol-6-amine, wherein the heteroaryl group is optionally substituted.

The term "heteroaryl," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, or sulfur, and wherein each ring in the system contains 3 to 7 ring members. The term "heteroaryl" may be used interchangeably with the term "heteroaryl ring" or the term "hetero aromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, a heteroaryl group may be substituted with up to three optional substituents. Suitable substituents on the unsaturated carbon atom of a heteroaryl group include: halogen; $C_{1-6}$alkyl; —OR°; —SR°; 1,2-methylenedioxy; 1,2-ethylenedioxy; phenyl (Ph), optionally substituted with R°; —O(Ph), optionally substituted with R°; —$(CH_2)_{1-2}$(Ph), optionally substituted with R°; —CH=CH(Ph), optionally substituted with R°; —$NO_2$; —CN; —$N(R°)_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(NOR°)R°; —S(O)$_2$R°; —S(O)$_3$R°; —S(O)$_2$N(R°)$_2$; —S(O)R°; —NR°S(O)$_2$N(R°)$_2$; —NR°S(O)$_2$R°; —N(OR°R°; —C(=NH)—N(R°)$_2$; —$(CH_2)_{0-2}$NHC(O)R°; -L-R°; -L-N(R°)$_2$; -L-SR°; -L-OR°; -L-($C_{3-10}$ cycloaliphatic), -L-($C_{6-10}$ aryl), -L-(5-10 membered heteroaryl), -L-(5-10 membered heterocyclyl), oxo, $C_{1-4}$haloalkoxy, $C_{1-4}$haloalkyl, -L-$NO_2$, -L-CN, -L-OH, -L-$CF_3$; or two substituents, on the same carbon or on different carbons, together with the carbon or intervening carbons to which they are bound, form a 5-7 membered saturated, unsaturated, or partially saturated ring, wherein L is a $C_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from hydrogen, optionally substituted $C_{1-6}$ aliphatic, an unsubstituted 5 to 6 membered heteroaryl or heterocyclic ring, phenyl, or —$CH_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Non-limiting optional substituents on the aliphatic group of R° include —$NH_2$, —$NH(C_{1-4}$ aliphatic), —$N(C_{1-4}$ aliphatic)$_2$, halogen, $C_{1-4}$ aliphatic, —OH, —$O(C_{1-4}$ aliphatic), —$NO_2$, —CN, —C(O)OH, —C(O)O($C_{1-4}$ aliphatic), —O(halo$C_{1-4}$ aliphatic), or halo$C_{1-4}$ aliphatic, wherein each of the foregoing $C_{1-4}$ aliphatic groups of R° is unsubstituted. In one embodiment, the heteroaryl is optionally substituted with up to 3 groups selected from fluoro, chloro, —$NH_2$, —$NH(C_{1-4}$ aliphatic), —$N(C_{1-4}$ aliphatic)$_2$, $C_{1-4}$ aliphatic, —OH, —$O(C_{1-4}$ aliphatic), —$NO_2$, —CN, —C(O)OH, —C(O)O($C_{1-4}$ aliphatic), —$O(C_{1-4}$ aliphatic) containing 1-3 fluorines, or $C_{1-4}$ aliphatic containing 1-3 fluorines.

As detailed above, in some embodiments, two independent occurrences of R° (or R⁺, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

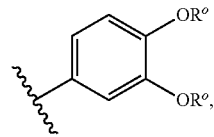

these two occurrences of R° are taken together with the oxygen atoms to which they are bound to form a fused 6-membered oxygen containing ring:

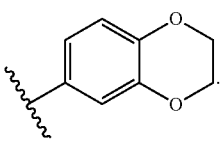

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

In another aspect, the invention features a pharmaceutical composition comprising Compound 1, in the anhydrous or dehydrate form, and a pharmaceutically acceptable carrier, adjuvant or vehicle. In one embodiment, the composition includes an additional chemotherapeutic or anti-proliferative agent, an anti-inflammatory agent, an agent for treating atherosclerosis, or an agent for treating lung fibrosis.

In another aspect, the invention features a method of treating or lessening the severity of a proliferative disorder in a patient comprising administering Compound 1 in an amount sufficient to treat or lessen the severity of a proliferative disorder in said patient. In one embodiment, the proliferative disorder is metastatic cancer. In another embodiment, the proliferative disorder is a glioblastoma; hepatocellular carcinoma, a gastric carcinoma; or a cancer selected from colon, breast, prostate, brain, liver, pancreatic or lung cancer.

In another embodiment, the proliferative disorder is a metastatic cancer.

Compositions, Formulations, and Administration of Compounds of the Invention

In another aspect, the invention provides a composition comprising an anhydrous or dihydrate form of Compound 1 and a pharmaceutically acceptable carrier, adjuvant, or vehicle. In one embodiment, the amount of compound in a composition of this invention is such that is effective to measurably inhibit c-Met in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with anhydrous or dihydrate forms of Compound 1, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of anhydrous or dihydrate forms of Compound 1 include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of anhydrous or dihydrate forms of Compound 1, it is often desirable to slow the absorption of these forms from subcutaneous or intramuscular injection. This may be accomplished by the use of a liquid suspension of crystalline or amorphous material with poor water solubility. The rate of absorption of an anhydrous or dihydrate form of Compound 1 then depends upon its rate of dissolution that, in turn, may depend upon crystal size and crystalline form. Alternatively, dissolving or suspending an anhydrous or dihydrate form of Compound 1 in an oil vehicle accomplishes delayed absorption of a parenterally administered compound form. Injectable depot forms are made by forming microencapsule matrices of an anhydrous or dihydrate form of Compound 1 in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping an anhydrous or dihydrate form of Compound 1 in liposomes or microemulsions that are compatible with body tissues.

Compositions for rectal or vaginal administration are preferably suppositories which can be prepared by mixing an anhydrous or dihydrate form of Compound 1 with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of anhydrous or dihydrate forms of Compound 1 include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of an anhydrous or dihydrate form of Compound 1 to the body. Such dosage forms can be made by dissolving or dispensing an anhydrous or dihydrate form of Compound 1 in the proper medium. Absorption enhancers can also be used to increase the flux of Compound 1 across the skin. The rate can be controlled by either providing a rate controlling membrane or by dispersing an anhydrous or dihydrate form of Compound 1 in a polymer matrix or gel.

Anhydrous or dihydrate forms of Compound 1 are preferably formulated in dosage unit form for ease of administration and uniformity of dosage. The expression "dosage unit form" as used herein refers to a physically discrete unit of agent appropriate for the patient to be treated. It will be understood, however, that the total daily usage of a Compound 1 and compositions comprising a Compound 1 will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of an anhydrous or dihydrate form of Compound 1 that may be combined with the carrier materials to produce a composition in a single dosage form will vary depending upon the host treated, the particular mode of administration. Preferably, the compositions should be formulated so that a dosage of from 0.01 to 100 mg/kg body weight/day of the inhibitor can be administered to a patient receiving these compositions. In one example, compositions are formulated such that the dosages of a Compound 1 are from 3 to 30 mg/kg body weight/day. In another example, compositions are formulated such that the dosages of a Compound 1 are from 5 to 60 mg/kg body weight/day.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compound 1 and Compositions Comprising the Compound 1

The term "c-Met" is synonymous with "c-MET," "cMet", "MET", "Met" or other designations known to one skilled in the art.

The term "c-Met-mediated disease" or "c-Met-mediated condition", as used herein, means any disease state or other deleterious condition in which c-Met is known to play a role.

The terms "c-Met-mediated disease" or "c-Met-mediated condition" also mean those diseases or conditions that are alleviated by treatment with a c-Met inhibitor. Such conditions include, without limitation, renal, gastric, colon, brain, breast, prostate, liver, pancreatic, or lung cancer, glioblastoma, atherosclerosis, or lung fibrosis.

According to one aspect, the invention features a method of inhibiting c-Met kinase activity in a patient comprising the step of administering to said patient an anhydrous or dihydrate form of Compound 1, or a composition comprising said compound.

In another aspect, the present invention features a method treating a proliferative disorder in a patient comprising the step of administering to the patient a therapeutically effective dose of an anhydrous or dihydrate form of Compound 1 or a composition comprising said form.

The proliferative disorder can be cancer, such as, for example, renal, gastric, colon, brain, breast, liver, prostate, and lung cancer, or a glioblastoma.

In another embodiment, the present invention relates to a method of treating or lessening the severity of hepatocellular carcinoma in a patient in need thereof, comprising administering to said patient an anhydrous or dihydrate form of Compound 1 or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient an anhydrous or dihydrate form of Compound 1 for a composition thereof.

Depending upon the particular condition, or disease, to be treated, additional therapeutic agents that are normally administered to treat that condition may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with an anhydrous or dihydrate form of Compound 1 to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycin, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), azaepothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), O6 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

In a further embodiment, the additional therapeutic agent is not metabolized by more than 90% by Cytochrome $P_{450}$ 3A4 (CYP3A4).

Those additional agents may be administered separately from a composition containing an anhydrous or dihydrate form of Compound 1 as part of a multiple dosage regimen. Alternatively, those agents may be part of a single dosage form, mixed together with an anhydrous or dihydrate form of Compound 1 in a single composition. If administered as part of a multiple dosage regime, the two active agents may be submitted simultaneously, sequentially or within a period of time from one another normally within five hours from one another.

The amount of both an anhydrous or dihydrate form of Compound 1 and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of an anhydrous or dihydrate form of Compound 1 can be administered. In one example, compositions are formulated such that the dosages of a Compound 1 are from 3 to 30 mg/kg body weight/day. In another example, compositions are formulated such that the dosages of a Compound 1 are from 5 to 60 mg/kg body weight/day.

In those compositions that comprise an additional therapeutic agent, that additional therapeutic agent and an anhydrous or dihydrate form of Compound 1 may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

An anhydrous or dihydrate form of Compound 1, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with an anhydrous or dihydrate form of Compound 1 are another embodiment of the present invention.

Preparation of the Compound of Formula I

In order that the invention described herein may be more fully understood, the following examples are set forth. It should be understood that these examples are for illustrative purposes only and are not to be construed as limiting this invention in any manner.

As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference. The following definitions describe terms and abbreviations used herein:

| | |
|---|---|
| Brine | a saturated solution of NaCl in water |
| BSA | bovine serum albumin |
| DMSO | dimethylsulfoxide |
| ESMS | electrospray mass spectrometry |
| EtOAc | ethyl acetate |
| EtOH | ethyl alcohol |
| HPLC | high performance liquid chromatography |
| LCMS | liquid chromatography-mass spectrometry |
| Me | methyl |
| MeOH | methanol |
| MTBE | methyl t-butylether |
| Ph | phenyl |

| | |
|---|---|
| RT | room temperature |
| TCA | trichloroacetic acid |
| THF | tetrahydrofuran |
| TFA | trifluoacetic acid |

EXAMPLE 1

Preparation of 3-(difluoro(quinolin-6-yl)methyl)-N-(1-methyl-1H-pyrazol-4-yl)-[1,2,4]triazolo[3,4-b][1,3,4]thiadiazol-6-amine (Compound 1)

As shown in step 1-i of Scheme 1,6-iodoquinoline (750 g, 2.94 mol) was loaded into a nitrogen-purged 22 L round bottom flask equipped with a mechanical stirrer, temperature probe, temperature readout, nitrogen inlet line, and a cooling bath. Anhydrous THF (5.25 L) was added and the resulting solution cooled to −27° C. using iPrOH/dry ice bath. i-PrMg-Cl.LiCl (2.45 L, 1.3 M in THF, 1.1 eq) was added over 1 hour 17 minutes via an addition funnel, maintaining the temperature between −26° C. and −29° C. The reaction mixture was then stirred for 2.5 hours with the temperature maintained between −20° C. and −29° C. The brown slurry was cooled to −53° C. over 25 min using an i-PrOH/dry ice bath and diethyl oxalate (469 g, 0.44 L, 1.1 eq) was added over 1 hour 15 minutes via an addition funnel, maintaining the temperature between −51° C. and −53° C. The resulting dark solution was allowed to warm up to RT overnight (~18 hours) to produce a mustard-colored slurry. A solution of ammonium chloride (500 g, 9.35 mol, 3.18 eq) in water (4.5 L) was prepared and cooled to 10° C. using an ice bath. The reaction mixture was transferred into the ammonium chloride solution over 37 minutes via a transfer line by pulling a slight vacuum on the 22 L flask containing the stirring ammonium chloride solution. Once transfer was completed, the ice bath was removed, EtOAc (3.75 L) was added, and stirring was initiated. After about 15 min, stirring was stopped and layers were allowed to separate. The aqueous phase (pH=8) was extracted with EtOAc (3.75 L). The two organic layers were combined and washed with NaCl solution (112 g in 2.5 L water). The organic phase was concentrated under vacuum at 25° C. to provide an oil (763 g), which was purified by silica gel chromatography (7:1 to 1:1 hexane/EtOAc). Fractions containing pure produce were combined and concentrated under vacuum to yield ethyl 2-oxo-2-(quinolin-6-yl)acetate as a brown oil (compound 1001, 503 g, 74.5% yield): $^1$H NMR (500 MHz, DMSO-$d_6$) δ 1.40 (t, 3H), 4.51 (q, 2H), 7.71 (dd, 1H), 8.21 (d, 1H), 8.24 (d, 1H), 8.68 (dd, 1H), 8.77 (dd, 1H), 9.11 (dd, 1H).

As shown in step 1-ii of Scheme 1, compound 1001 (282 g, 1.23 mol) and DCM (2.82 L) were combined in a 12 L nitrogen-purged round bottom flask equipped with a mechanical stirrer, nitrogen inlet, temperature probe, and room temperature water bath. To the resulting solution was added bis-(2-methoxyethyl)aminosulfur trifluoride (DeoxoFluor™, 615 g, 0.50 L, 2.26 eq) over 45 minutes via an addition funnel. Absolute EtOH (12.8 g, 15 mL, 0.21 eq) was added via syringe in portions over 3 minutes and the reaction allowed to stir overnight at ambient temperature. In-process samples were taken, worked-up, and analyzed by $^1$H-NMR in order to monitor the progress of the reaction. Typical starting material to product molar ratio after the first ethanol addition was about 2:3. Accordingly, additional EtOH portions (12.3 g, 0.2 eq) were sequentially added via syringe with periods of 10 to 20 hours between additions until the observed starting material content was lower than 10%. A quench solution was prepared by mixing sodium bicarbonate (827 g, 8 equiv.) in water (8.3 L) and cooling to to 13° C. in an ice bath. The reaction mixture was transferred into the sodium bicarbonate quench solution over 0.5 hour via a transfer line by pulling vacuum on the 22 L flask containing the stirring sodium bicarbonate solution. Vigorous gas evolution was observed. The temperature was maintained between 10° C.-13° C., during the quench, after which time the ice bath was removed and the mixture stirred for 2 hours at 12° C.-15° C. The DCM layer was separated and the aqueous layer extracted with DCM (2×1 L). The DCM layers were combined and concentrated at 26° C. under vacuum to give 349 g of crude oil which was purified by silica chromatography (7:1 to 4:1 hexane/EtOAc). Fractions containing pure product were combined and concentrated to give an oil, which was taken up in 2×180 mL abs. EtOH and concentrated by rotary evaporation to yield ethyl 2,2-difluoro-2-(quinolin-6-yl)acetate as an oil (compound 1002, 164 g, 53% yield): $^1$H NMR (500 MHz, DMSO-$d_6$) δ 1.24 (t, 3H), 4.35 (q, 2H), 7.67 (dd, 1H), 7.91 (dd, 1H), 8.20 (d, 1H), 8.37 (s, 1H), 8.60 (d, 1H), 9.05 (dd, 1H); $^{19}$F NMR (470 MHz, DMSO-$d_6$) δ −101.2.

As shown in step 1-iii of Scheme 1, to a 1 L round-bottomed flask equipped with a stir bar and thermocouple was added compound 1002 (164 g, 633.9 mmol) and EtOH (398 mL). The yellow solution was cooled to 0° C. using an ice/water bath. Sodium hydroxide (570.5 mL of 2 M aqueous solution, 1.141 mol) was added slowly over 1 hour to the reaction mixture whilst maintaining the internal temperature below 20° C. The ice/water bath was removed and the mixture stirred at room temp for 2 hours. The reaction mixture was concentrated in vacuo and the yellow solid dried in a vacuum oven (50° C., 20-25 mm Hg, $N_2$ sweep) to give sodium 2,2-difluoro-2-(quinolin-6-yl)acetate (compound 1003, 156.0 g, 99% yield): $^1$H NMR (500 MHz, DMSO-$d_6$) δ 7.50-7.55 (dd, 1H), 7.90-7.85 (dd, 1H), 8.10-8.15 (d, 1H), 8.10 (s, 1H), 8.40-8.45 (d, 1H), 8.95-8.90 (dd, 1H); $^{19}$F NMR (470 MHz, DMSO-$d_6$) δ −98.15.

As shown in step 1-iv of Scheme 1, to a 3 L round-bottom flask equipped with a heating mantel, reflux condenser, thermocouple, mechanical stirrer, and purged with $N_2$ was added compound 1003 (98.6 g, 326.4 mmol), 1,3-dimethyl-2-imidazolidinone (1.607 L), and pyridine (38.73 g, 39.60 mL, 489.6 mmol). 50% propanephosphonic acid anhydride (T3P®) in 2-methyltetrahydrofuran (415.4 g, 652.8 mmol) was added in a single portion and a 15-20° C. exotherm was observed. The reaction mixture was heated to 70° C. for 1 hour, at which time thiocarbohydrazine (53.03 g, 489.6 mmol) was added in one portion. The reaction mixture was stirred for an additional 3 hours and then an additional portion of 50% T3P in 2-MeTHF (207.7 g, 326.4 mmol) was added, followed by stirring at 70° C. overnight. The reaction mixture was cooled to room temperature. In a separate flask, a solution of sodium bicarbonate (219.3 g, 2.611 mol) in water (2.41 L) was cooled using an ice/water bath. The reaction mixture was slowly added to the quench solution via cannula over 45 minutes, during which time foaming and precipitation of the product were observed. The solution was stirred at 5° C. for an additional hour at pH=7. The resulting solids were collected by suction filtration and the cake washed with water (3.2 L) and MTBE (3.2 L). The white solid was dried in a vacuum oven (50° C., 20-25 mm Hg) to give 4-amino-5-(difluoro (quinolin-6-yl)methyl)-4H-1,2,4-triazole-3-thiol compound 1004, 57 g, 58% yield): $^1$H NMR (500 MHz, DMSO-$d_6$) δ 5.70-5.65 (s, 2H), 7.50-7.55 (dd, 1H), 7.90-7.85 (dd, 1H), 8.10-8.15 (d, 1H), 8.10 (s, 1H), 8.40-8.45 (d, 1H), 8.95-8.90 (dd, 1H), 14.3-14.25 (s, 1H); $^{19}$F NMR (470 MHz, DMSO-d$_6$) δ −92.50.

As shown in step 1-v of Scheme 1, triphenylphosphine (17.66 g, 67.35 mmol), 1,1,1,2,2,2-hexachloroethane (15.94 g, 67.35 mmol), compound 1004 (13.37 g, 44.90 mmol) were combined in a 500 mL round bottom flask fitted with a mechanical stirrer, thermocouple, under an atmosphere of nitrogen. Anhydrous acetonitrile (461.0 mL) was added followed by the addition of Et$_3$N (14.09 g, 19.41 mL, 139.2 mmol) to the stirred mixture whilst maintaining the temperature between 21.4-25.1° C. The reaction mixture became a clear solution and then became a slurry once the product formed (within about 2 minutes). Water (808.9 mg, 808.9 μL, 44.90 mmol) was then added followed by the addition of MeOH (14.39 g, 18.19 mL, 449.0 mmol) and the reaction then stirred for additional 45 min. The solid was collected by filtration and the cake washed with CH$_3$CN (132 mL). The cake was dried in a vacuum oven at 45° C. with a nitrogen bleed to produce 5-(difluoro(quinolin-6-yl)methyl)-4-(iminotriphenylphosphorano)-4H-1,2,4-triazole-3-thiol (compound 1005, 25.57 g, 98.8% yield) as a beige solid: $^1$H NMR (400 MHz, DMSO-d$_6$) δ 7.51-7.42 (m, 6H), 7.70-7.56 (m, 12H), 8.11 (d, 1H), 8.16 (m, 1H), 8.49 (dd, 1H), 9.03 (dd, 1H), 13.64 (br s, 1H). $^{19}$F NMR (376 MHz, DMSO-d$_6$) δ −91.77. $^{31}$P NMR (162 MHz, DMSO-d$_6$) δ 19.71.

As shown in step 1-vi of Scheme 6, to a 2 L, 4-necked, round-bottomed flask fitted with overhead stirrer, thermocouple, reflux condenser, and nitrogen bubbler was added 1-methylpyrazole-4-carboxylic acid (27.33 g, 216.7 mmol). Toluene (600 mL) and triethylamine (30.70 g, 42.29 mL, 303.4 mmol) were added at 20.1° C. with no observed temperature increase. The resulting white slurry became a colorless solution after heating to 103° C. Diphenylphsophoryl azide (DPPA, 61.48 g, 48.14 mL, 216.7 mmol) was added over a period of 30 minutes, keeping the temperature at between 103.1 and 107° C. Heating was discontinued and allowed to cool to room temperature. The resulting 4-isocyanato-1-methyl-1H-pyrazole was not isolated and instead to it was added compound 1005 (120 g, 216.7 mmol) in one portion at room temperature. Analytical HPLC analysis immediately after the addition showed 51.2% conversion of the starting material to Compound 1. Starting with 216.7 mmol of 1-methylpyrazole-4-carboxylic acid, additional 4-isocyanato-1-methyl-1H-pyrazole was prepared as indicated above in a separate flask. After cooling to room temperature, this reaction mixture was transferred to the first reaction mixture via cannula. HPLC analysis indicated 100% conversion after addition. EtOAc (240 mL) was added to the reaction mixture and a white precipitate formed. The reaction was stirred for 30 minutes and the solid collected by suction filtration. The cake [(comprising 1-(3-(difluoro(quinolin-6-yl)methyl)-[1,2,4]triazolo[3,4-b][1,3,4]thiadiazol-6-yl)-1,3-bis(1-methyl-1H-pyrazol-4-yl)urea (compound 1006) as a by-product] was washed with EtOAc (600.0 mL). The filtrate was concentrated in vacuo by rotary evaporation at 35° C. to give 272.4 g of a brown oil. The oil was dried under high vacuum and was purified by column chromatography, using an 8:1 ratio of SiO$_2$ to crude oil and eluting with a gradient of 1% to 5% EtOH in DCM to produce 3-(difluoro(quinolin-6-yl)methyl)-N-(1-methyl-1H-pyrazol-4-yl)-[1,2,4]triazolo[3,4-b][1,3,4]thiadiazol-6-amine (Compound 1, 111 g), which was further purified by crystallization. Accordingly, a 33.5 g portion of this material to 250 mL 3-neck round bottom flask fitted with mechanical stirrer and nitrogen bubbler. The solid was an orange-tan color. A total of 135 mL of CH$_3$CN was added to give a thick slurry. After 2.5 hours, the solids were collected by suction filtration after 3 hours. The wet cake was washed with CH$_3$CN (67 mL) to give 13.9 g of wet solid. Vacuum drying was carried out (43° C., 20-25 in Hg, N$_2$ sweep) over 15.5 hours to give 10.25 g of pure Compound 1, anhydrous form (>99.9% purity by HPLC analysis, <0.1% PPh$_3$O). The MeCN filtrate was treated with equal amount of water. A solid precipitated and the slurry was stirred for 2 hours. The solid was collected by suction filtration. The wet cake was washed with 35 mL water. The cake was dried (43° C., 20-25 in Hg, N$_2$ sweep) to give 9.5 g of a solid material, which was treated with CH$_3$CN as above to provide an additional 4.78 g of pure Compound 1 (anhydrous form, total=15.03 g, 57.7% overall yield from compound 1005). The yield can be increased further by aminolyzing the urea side product (compound 1006) with NH$_3$/MeOH to recover additional Compound 1.

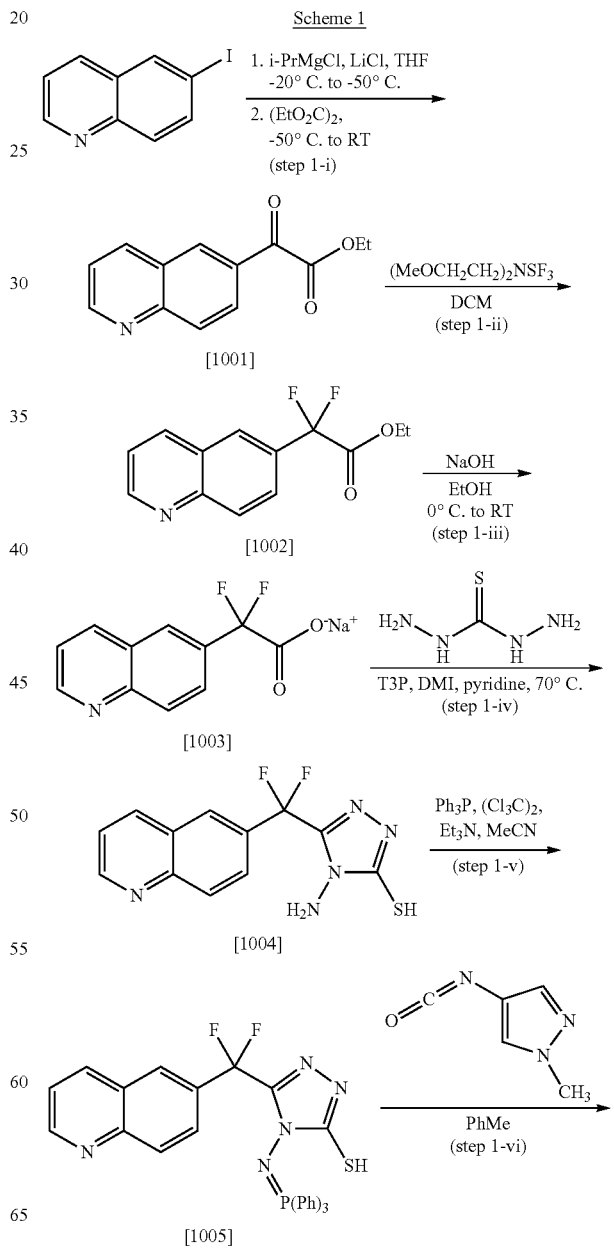

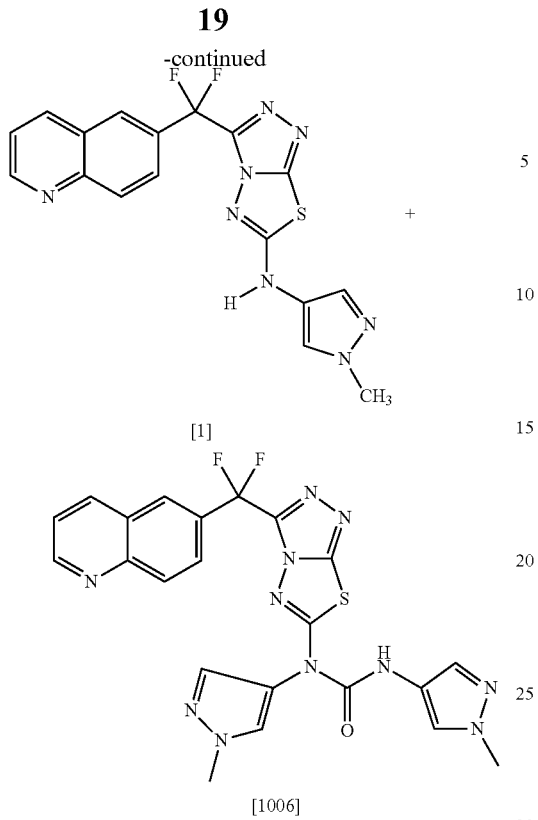

[1]

[1006]

X-ray powder diffraction (XRPD) of the anhydrous form of Compound 1 showed peaks at 5.0, 9.8, 12.9, 16.8, 19.3, 20.0, 21.2, 21.8, 22.5, 25.9, 26.2, 26.8, 28.5, 29.4, 30.7, 32.5, and 35.5 (2-theta scale). Differential scanning calorimetry (DSC) showed a single melting endotherm at 211° C. Thermogravimetric analysis (TGA) indicated that this neat form A had less than a 0.3% weight loss upon heating to 150° C.

Compound 1, anhydrous form A (225 g) was charged to a 22 L reactor fitted with a mechanical stirrer and nitrogen bubbler. Water (9 L, 40 vol) was added and the thick slurry stirred at room temperature. Over the next 4 hours, 1-4 L portions of water (total 13 L, 60 vol) were added to keep the slurry stirring. The solids were collected by suction filtration and the cake washed with water (900 mL, 4 vol). The material was dried (45° C., 20-25 in. Hg, $N_2$ sweep) for 3 days in an oven containing a water dish to raise the humidity in the oven. Compound 3 dihydrate (242.9 g) was isolated as a beige solid. XRPD of the dihydrate showed peaks at 6.1, 7.0, 8.0, 13.4, 13.9, 15.5, 18.1, 20.0, 21.1, 23.5, 23.7, 24.7, 26.4, and 27.0 (2-theta scale). The DSC thermogram showed multiple endotherms below 125° C., attributed to the loss of the associated water with compound 3, followed by a sharp exotherm at about 135° C., indicating conversion to neat form A—which subsequently melted at 211° C. The TGA thermogram confimed a weight loss of about 7% upon heating to about 125° C., indicating that the material was a dihydrate. $^1$H NMR analysis (300 MHz, DMSO-$d_6$) showed peaks at δ 10.63 (s, 1H), 9.04 (dd, J=4.1, 1.5 Hz, 1H), 8.59 (d, J=8.1 Hz, 1H), 8.47 (s, 1H), 8.20 (d, J=8.8 Hz, 1H), 7.98 (dd, J=8.9, 2.0 Hz, 1H), 7.75-7.54 (m, 2H), 7.42 (s, 1H), 3.78 (s, 3H).

Biological Assay of Compound 1

EXAMPLE 3 c-Met Kinase Inhibition Assay

Compound 1 was screened for its ability to inhibit c-Met kinase using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 μL per well containing 0.5 nM c-Met, 100 mM HEPES (pH 7.5), 10 mM $MgCl_2$, 25 mM NaCl, 0.01% BSA, 1 mM DTT, 0.5 mg/mL polyE4Y, and 35 μM ATP. Accordingly, Compound 1 was dissolved in DMSO to make a 10 mM initial stock solution. Serial dilutions in DMSO were then made to obtain the final solutions for the assay. A 1.5 μL aliquot of DMSO or inhibitor in DMSO was added to each well, followed by the addition of $^{33}$P-ATP, and finally the addition of c-Met and polyE4Y (obtained from Sigma). After 20 min, the reaction was quenched with 50 μL of 30% trichloroacetic acid (TCA) containing 4 mM ATP. The reaction mixture was transferred to the 0.66 mm GF filter plates (Corning) and washed three times with 5% TCA. Following the addition of 50 μL of Ultimate Gold™ high efficiency scintillant (Packard Bioscience), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. Compound 1 had a $K_i$ value for the inhibition of c-Met of less than 20 nM.

EXAMPLE 4

Inhibition c-Met Activity in Snu5 Gastric Carcinoma Cells

Compound 1 was also screened for its ability to inhibit the Luciferase-induced signal in an engineered Snu5 cell line. Snu5 [obtained from American Type Culture Collection (Catalog number CRL-5973)] is a human gastric carcinoma known to overexpress c-Met, which is constitutively active. The cell line was transduced with the retrovirus, pCLPCX, which contains a genetic construct consisting of 6×AP1 promoter response elements and a luciferase gene having a C-terminal PEST sequence (proteolytic signal from mouse ornithine decarboxylase, which reduces the half-life of the luciferase). The constitutively active c-Met activates cellular pathways (principally MAP kinase), resulting in AP-1-induced transcription of luciferase-PEST and translation into the final product, the activity of which is quantifiable as a chemiluminescent readout upon the addition of luciferin (Steady-Glo from Promega.). Residual luminescence is strongly correlated to the inhibition of c-Met. A stable cell line was obtained by selecting the new cell line (Snu5-AP1-Luc-Pest) with puromycin. The cells were grown in complete media [Iscove's media (Invitrogen) containing 10% fetal bovine serum (FBS, Hyclone) and penicillin/gentamycin (Invitrogen)]. Compound 1 was dissolved in DMSO to make 10 mM initial stock solutions. Serial dilutions in DMSO were then made and transferred to complete medium to make a 10× solution. The Snu5-AP1-Luc-Pest cells were counted and diluted to 200,000-cells/mL solution. The cells (90 μL) were added to each well in a 96-well black with clear bottom plate (Costar). Then 10 μL of the 10× compound solution was added to the cells in triplicate. The plates were incubated in a 37° C./5% $CO_2$ incubator. After 6 hours, 50 μL of the Steady-Glo reagent (Promega) was added to each well and placed on a plate shaker for 5 minutes to ensure that the cells were completely lysed. The plate was read on a 1450 Microbeta Liquid Scintillation and Luminescence Counter (Perkin-Elmer). Compound 1 had an $IC_{50}$ value for the inhibition c-Met activity in Snu5 gastric carcinoma cells of less than 20 nM.

EXAMPLE 5

Inhibition of Tumor Growth in a Mouse Model

Compound 1 was investigated for its ability to inhibit tumor growth of subcutaneously implanted SNU-5 gastric cancer cells in severe combined immunodeficient (SCID) mice. SNU-5 cells (CRL-5973, American Type Culture Collection, Manassas, Va.) were cultured in ISCOVE's Modified Dulbecco's Medium (IMDM) (Invitrogen, Carlsbad, Calif.) supplemented with 10% fetal bovine serum (FBS) (Hyclone, Logan, Utah), 100 units/mL of penicillin, 100 mg/mL of streptomycin (Invitrogen, Carlsbad, Calif.), and 2 mM L-glutamine. Cells were cultured for fewer than 4 passages prior to implantation. Female SCID mice (Fox Chase SCID, CB-17, mice weighing 17 to 19 g obtained from Charles River Laboratories, Wilmington, Mass.) were injected subcutaneously (s.c.) with $5 \times 10^6$ SNU-5 cells into the right dorsal axillary region on Day 0. Treatments were initiated on Day 25 when the average tumor volume reached approximately 358 mm$^3$.

Compound 1, formulated in a vehicle containing 30% (w/v) Propylene Glycol and 10% Solutol (Sigma-Aldrich, St Louis, Mo.) as a suspended homogenous form, was administered orally (p.o.) once daily (QD) at total daily doses of 3, 10, and 30 mg/kg/day for 14 days. Tumor volumes (calculated using the ellipsoid formula, (length$\times$width$^2$)/2, where length and width represented the largest and smallest dimensions of the tumor, respectively) were recorded for two weeks after the initiation of treatment. The study was terminated 38 days after tumor implantation. Average tumor volumes are presented in Table 1. Tumor weights at the termination of the study are presented in Table 2.

TABLE 1

SNU-5 tumor volumes*

|  | Day 25 | Day 28 | Day 31 | Day 35 | Day 38 |
| --- | --- | --- | --- | --- | --- |
| Vehicle control | 357.6 ± 36.7 | 487.1 ± 45.8 | 578.4 ± 66.0 | 753.2 ± 77.9 | 937.1 ± 101.0 |
| Compound 3, 30 mg/kg/day | 359.5 ± 35.1 | 281.3 ± 28.7 | 256.5 ± 23.6 | 255.7 ± 21.1 | 273.4 ± 24.2 |
| Compound 3, 10 mg/kg/day | 358.0 ± 17.1 | 354.2 ± 21.7 | 381.8 ± 25.6 | 406.6 ± 23.4 | 453.9 ± 27.3 |
| Compound 3, 3 mg/kg/day | 356.1 ± 24.5 | 432.6 ± 31.2 | 511.9 ± 36.3 | 587.8 ± 39.5 | 670.4 ± 46.2 |

*tumor volume measurements are in mm$^3$ and are reported as mean ± standard error

TABLE 2

SNU-5 tumor weights at study termination

| Animal ID | Vehicle, 10 mL/kg | Compound 3 30 mg/kg/day | Compound 3 10 mg/kg/day | Compound 3 3 mg/kg/day |
| --- | --- | --- | --- | --- |
| 1 | 863 | 350 | 275 | 508 |
| 2 | 838 | 327 | 305 | 368 |
| 3 | 896 | 150 | 371 | 679 |
| 4 | 974 | 246 | 309 | 596 |
| 5 | 857 | 180 | 319 | 619 |
| 6 | 1607 | 173 | 476 | 505 |
| 7 | 760 | 260 | 358 | 525 |
| 8 | 629 | 420 | 469 | 485 |
| 9 | 896 | 250 | 279 | 605 |
| 10 | 1151 | 156 | 660 | 655 |
| 11 |  |  | 418 | 851 |
| 12 |  |  | 400 | 770 |
| 13 |  |  | 387 | 405 |
| 14 |  |  | 410 | 790 |
| 15 |  |  | 349 | 938 |
| Mean | 947.1 | 251.2 | 385.7 | 619.9 |
| SD | 268.0 | 91.0 | 98.2 | 163.5 |
| SE | 84.7 | 28.8 | 25.4 | 42.2 |

As shown in Tables 1 and 2, Compound 1 demonstrated significant and dose-dependent anti-tumor activity at all three dose levels tested. A dose of 30 mg/kg/day resulted in tumor regression of −23.9% (P<0.001) by tumor volume analysis. Tumors harvested from the 3, 10, and 30 mg/kg/day VRT-846198 treatment groups were significantly smaller than those harvested from the vehicle control group, with percent weight reductions of 34.5%, 59.3%, and 73.5%, respectively (all P<0.002).

EXAMPLE 6

Inhibition of Tumor Metastasis in Mouse Model

Compound 1 was investigated for its ability to inhibit the metastasis of subcutaneously implanted tumors to the lungs of severe combined immunodeficient (SCID) mice. Accordingly, A549 cells (A549HGF-lm1115, transfected with hepatocyte growth factor, luciferase, and green fluorescent protein) were cultured in RPMI1640 medium (Invitrogen, Carlsbad, Calif.) supplemented with 10% fetal bovine serum (FBS) (Hyclone, Logan, Utah), 100 units/mL of penicillin, 100 mg/mL of streptomycin (Invitrogen, Carlsbad, Calif.), and 2 mM L-glutamine for fewer than 4 passages prior to implantation. 3-(Difluoro(quinolin-6-yl)methyl)-N-(1-methyl-1H-pyrazol-4-yl)-[1,2,4]triazolo[3,4-b][1,3,4]thiadiazol-6-amine (Compound 1) was formulated in a vehicle containing 0.5% (w/v) methylcellulose (Sigma-Aldrich, St Louis, Mo.) and 0.1% (v/v) Tween 80™ as a dissolved homogenous form, which was prepared fresh each day and administered to mice via oral gavage at a dosing volume of 10 mL/kg.

Female SCID mice were injected subcutaneously (s.c.) with $5 \times 10^6$ A549HGF cells into the right dorsal axillary region on Day 0. Treatments were initiated on the same day by oral administration (p.o.) of Compound 1 once daily (QD) at total daily doses of 30 and 60 mg/kg/day for 22 days. Ectopic tumor measurements were recorded twice a week for 3 weeks after the initiation of treatment. Compound 3 was found to result in no significant change in primary A549 tumor cell growth at the site of implantation for mice dosed at 30 or 60 mg/kg/day vs. the tumor cell growth in mice dosed with vehicle alone.

In order to evaluate the anti-metastatic potential of Compound 1, at the termination of the study all animal lung tissues were harvested and lysed by homogenization for ex vivo quantification via luciferase luminescence. Table 3 illustrates the tumor cell content in lung tissue at study termination and the data therein indicate that Compound 1 significantly inhibits the formation of lung metastases in mice treated with Compound 1 at 60 mg/kg/day (average fluorescent count of 6672.3±1986.1 SEM) compared to vehicle controls (average fluorescent count of 23531.5±8278.2 SEM, p<0.02).

TABLE 3

Luminescence of homogenized lung tissue in SCID mice treated with Compound 1 vs. control animals treated with only vehicle

| Animal ID | Vehicle, 10 mL/kg (counts) | Compound 1 30 mg/kg/day (counts) | Compound 1 60 mg/kg/day (counts) |
|---|---|---|---|
| 1 | 6610 | 16300 | 4860 |
| 2 | 2980 | 5640 | 2470 |
| 3 | 1850 | 3890 | 2170 |
| 4 | 4300 | 5270 | 1480 |
| 5 | 21300 | 2270 | 2540 |
| 6 | 53200 | 2620 | 19300 |
| 7 | 9670 | 17200 | 21100 |
| 8 | 22600 | 21300 | 3800 |
| 9 | 26700 | 6430 | 16500 |
| 10 | 13300 | 4340 | 1440 |
| 11 | 112000 | 65400 | 2620 |
| 12 | 19300 | 2230 | 2920 |
| 13 | 12100 | | 5540 |
| Mean | 23531.5 | 12740.8 | 6672.3 |
| standard deviation | 29884.3 | 17828.3 | 7169.7 |
| standard error | 8278.2 | 5146.7 | 1986.1 |

All publications and patents cited in this specification are herein incorporated by reference as if each individual publication or patent were specifically and individually indicated to be incorporated by reference. Although the foregoing invention has been described in some detail by way of illustration and example for purposes of clarity or understanding, it will be readily apparent to those of ordinary skill in the art in light of the teachings of this invention that certain changes and modifications may be made thereto without departing from the spirit or scope of the appended claims.

What is claimed is:
1. A compound having the formula:

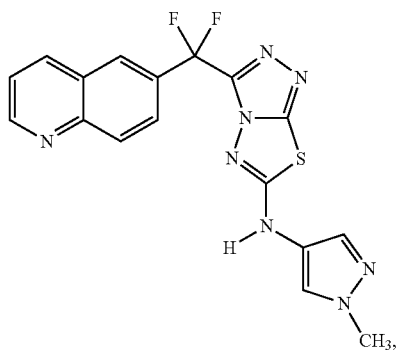

(1)

said compound being in an anhydrous form.
2. A compound according to claim 1, wherein said compound has a crystalline form characterized by X-ray powder diffraction (XRPD) peaks at 5.0, 9.8, 12.9, 16.8, 19.3, 20.0, 21.2, 21.8, 22.5, 25.9, 26.2, 26.8, 28.5, 29.4, 30.7, 32.5, and 35.5 (2-theta scale).
3. A compound having the formula:

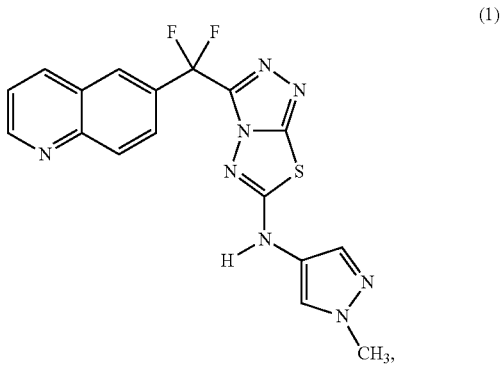

(1)

said compound being in a dihydrate form.
4. A compound according to claim 3, wherein said compound has a crystalline form characterized by X-ray powder diffraction (XRPD) peaks at 6.1, 7.0, 8.0, 13.4, 13.9, 15.5, 18.1, 20.0, 21.1, 23.5, 23.7, 24.7, 26.4, and 27.0 (2-theta scale).
5. A pharmaceutical composition comprising a compound according to claim 1 and a pharmaceutically acceptable carrier, adjuvant or vehicle.
6. The composition according to claim 5, additionally comprising a chemotherapeutic or anti-proliferative agent, an anti-inflammatory agent, an agent for treating atherosclerosis, or an agent for treating lung fibrosis.
7. A method of treating or lessening the severity of a proliferative disorder in a patient comprising administering the compound according to claim 1, or a pharmaceutical composition comprising said compound, in an amount sufficient to treat or lessen the severity of said proliferative disorder in said patient.
8. The method according to claim 7, wherein said disorder is metastatic cancer.
9. The method according to claim 7, wherein said disorder is a glioblastoma; a gastric carcinoma; or a cancer selected from colon, breast, prostate, brain, liver, pancreatic or lung cancer.
10. The method according to claim 7, wherein said disorder is hepatocellular carcinoma.
11. A method of preparing 3-(difluoro(quinolin-6-yl)methyl)-N-(heteroaryl)-[1,2,4]triazolo[3,4-b][1,3,4]thiadiazol-6-amines, said method comprising treating sodium 2,2-difluoro-2-(quinolin-6-yl)acetate with thiocarbohydrazine in the presence of propanephosphonic acid anhydride to produce 4-amino-5-(difluoro(quinolin-6-yl)methyl)-4H-1,2,4-triazole-3-thiol; reacting 4-amino-5-(difluoro(quinolin-6-yl)methyl)-4H-1,2,4-triazole-3-thiol with triphenylphosphine to produce 5-(difluoro(quinolin-6-yl)methyl)-4-(iminotriphenylphosphorano)-4H-1,2,4-triazole-3-thiol; and reacting 5-(difluoro(quinolin-6-yl)methyl)-4-(iminotriphenylphosphorano)-4H-1,2,4-triazole-3-thiol with an isocyanto heteroaromatic compound to produce a 3-(difluoro(quinolin-6-yl)methyl)-N-(heteroaryl)-[1,2,4]triazolo[3,4-b][1,3,4]thiadiazol-6-amine, wherein said heteroaryl group is optionally substituted with up to 3 groups selected from fluoro, chloro, —NH$_2$, —NH(C$_{1-4}$ aliphatic), —N(C$_{1-4}$ aliphatic)$_2$, C$_{1-4}$ aliphatic, —OH, —O(C$_{1-4}$ aliphatic), —NO$_2$, —CN, —C(O)OH, —C(O)O(C$_{1-4}$ aliphatic), —O(C$_{1-4}$ aliphatic) containing 1-3 fluorines, or C$_{1-4}$ aliphatic containing 1-3 fluorine.

* * * * *